United States Patent [19]
Henning et al.

[11] Patent Number: 5,736,407
[45] Date of Patent: Apr. 7, 1998

[54] PROCESS FOR DETERMINING THE THICKENING EFFECT OF SILICON DIOXIDE

[75] Inventors: Thomas Henning, Gelnhausen; Guenther Michael, Karlstein; Guenter Stadtmueller, Alzenau, all of Germany

[73] Assignee: Degussa Aktiengesellschaft, Frankfurt, Germany

[21] Appl. No.: 780,450

[22] Filed: Jan. 8, 1997

Related U.S. Application Data

[63] Continuation-in-part of Ser. No. 364,192, Dec. 27, 1994, abandoned.

[30]  Foreign Application Priority Data

Jan. 5, 1994 [DE] Germany ............... 44 00 170.3

[51] Int. Cl.⁶ .................................................. G01N 21/49
[52] U.S. Cl. ................. 436/72; 436/164; 73/61.42
[58] Field of Search ................... 436/72, 164, 909; 356/336, 339; 73/64.43, 61.42

[56]  References Cited

U.S. PATENT DOCUMENTS

| | | | |
|---|---|---|---|
| 4,067,954 | 1/1978 | Volling | 423/336 |
| 4,542,171 | 9/1985 | Elser et al. | 523/201 |
| 4,889,815 | 12/1989 | Bradwell et al. | 436/909 X |
| 5,370,892 | 12/1994 | El-Nokaly et al. | 426/531 |

OTHER PUBLICATIONS

Hackh's Chemical Dictionary, 4th ed. Mc Graw-Hill Book Co. (1969), p. 450.

Ullmann's Encyclopedia, 5th Edition, vol. A23, pp. 635-642, no date.

Messen, Steuern und Regeln in der Chemischen Technik, J. Hengstenberg et al. 1980, Band II, pp. 56-58.

*Primary Examiner*—Jeffrey Snay
*Attorney, Agent, or Firm*—Beveridge, DeGrandi, Weilacher & Young, LLP

[57]  ABSTRACT

The thickening effect of flame hydrolysis produced silicon dioxide is determined by making a dispersion of the flame hydrolysis produced silicon dioxide in a liquid such as water or ethanol and measuring the turbidity of this dispersion.

9 Claims, 3 Drawing Sheets

PROCESS FOR DETERMINING THE THICKENING EFFECT OF SILICON DIOXIDE

REFERENCE TO RELATED APPLICATION

This application is a continuation-in-part of our application having Ser. No. 08/364,192 filed Dec. 27, 1994, now abandoned.

INTRODUCTION AND BACKGROUND

The present invention relates to a process for determining the thickening effect of silicon dioxide.

Synthetically prepared silicon dioxide, in particular silicon dioxide which is prepared from $SiCl_4$ by flame hydrolysis, as described for example in Ullmann's Enzyklopädie, 4th ed., vol. 21, page 464 et seq., is used inter alia as a thickening agent in lacquers, paints, or resin solutions.

In addition to the thickening effect, determination of the BET surface area is used to determine the characteristics of silicon dioxide produced by flame hydrolysis during the production thereof.

It has been shown, however, that it being not possible to draw conclusions about the thickening effect of the silica from the BET surface area which is measured, because there is no direct correlation with the thickening effect. Thus, silicon dioxides produced by flame hydrolysis which have the same BET surface areas exhibit differing thickening effects. Also, synthetic silicas with different BET surface areas may have the same thickening effect. This discrepancy means that determining the BET surface area during the flame hydrolysis production process of silicon dioxide cannot be used as the sole criterion to determine the nature and quality of the product produced thereby.

Therefore it is necessary to find a method of determination, for use during the flame-hydrolysis production process, by means of which it is possible to provide reliable quality control of the resulting silicon dioxide and its capability to act as a suitable thickening agent.

SUMMARY OF THE INVENTION

The invention provides a process for determining the thickening effect of silicon dioxide which has been produced by the flame hydrolysis method by forming a dispersion of the flame-hydrolysis-produced silicon dioxide in an inert liquid medium such as water or in a lower alcohol such as ethanol and then measuring the turbidity of this dispersion by standard turbidity measurement determinations.

BRIEF DESCRIPTION OF DRAWINGS

The present invention will be further understood with reference to the drawings, wherein.

DETAILED DESCRIPTION OF INVENTION

Figure 1:
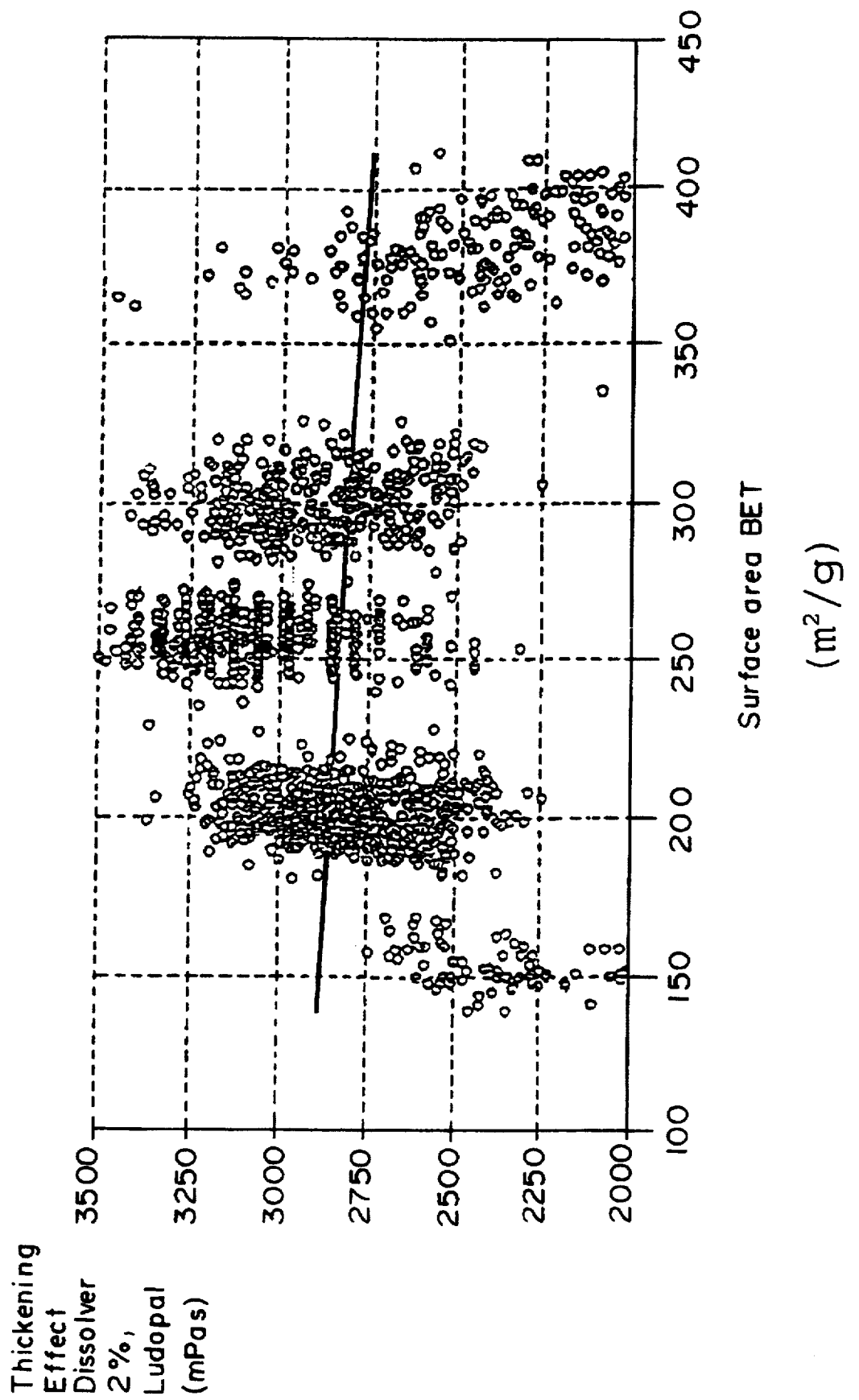
FIG. 1 is a plot of data measuring the thickening effect versus surface area of flame hydrolysis produced silica.

It is known in the art that very finely divided oxides can be produced by the hydrolytic conversion of a volatile metal halide. The volatile halide is mixed with a combustible gas and air or oxygen. The resulting mixture is then fed to a burner where combustion takes place. In the alternative, the volatile halide, combustible gas, and air or oxygen can be fed separately to the burner. The combustible gas contains hydrogen, and the air or oxygen are mixed with the combustible gas in such a ratio that the hydrogen will be almost completely burned, and a quantity of water vapor formed which will at least suffice for the hydrolysis of the volatile halide. For the production of particularly active products, the temperature of the flame is conveniently controlled by the addition of hyperstoichiometric quantities of air or oxygen or of an inert gas, such as nitrogen.

The products obtained according to these known processes are generally obtained together with a waste gas containing a hydrogen halide gas. The product, in the form of oxide particles, can be isolated from the hydrogen halide gas in a separator.

When chlorides, such as silicon tetrachloride, are used as the volatile halide, the hydrolysis or pyrolysis takes place generally in accordance with the following equation:

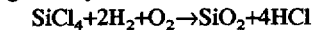

$SiCl_4 + 2H_2 + O_2 \rightarrow SiO_2 + 4HCl$

Methods for production are known in the art, as shown for example in U.S. Pat. Nos. 3,954,945 and 4,067,954.

The product is an amorphous silica which, due to its unique manufacturing process (hydrolysis of silicon tetrachloride in an oxygen-hydrogen flame), represents a silicon dioxide aerosol formed by coagulated spherical particles. These spherical particles have an average diameter of only 10 to 20 nanometers. How extremely small the silica particles are becomes evident when comparing them with the wave-length of the visible light which is 400 to 700 nanometers. As a result of the minute particles, the silica has an extremely large specific surface area (i.e. surface area per weight unit), preferentially being determined by the nitrogen absorption method of Brunauer, Emmett, and Teller (BET surface area) and varying from 50 to 400 $m^2/g$ depending on the grade.

The surface of the silica particles is relatively smooth and consists of the boundary surface of a three-dimensional network of siloxane groups (—Si—O—Si—O—). Some of the silicon atoms on the surface, however, are only bound to three silicon atoms via siloxane bonds; the fourth valence is saturated by an OH-group, thus forming a so-called silanol group (—Si—OH). The silanol groups and their number per unit surface area (i.e. silanol group density per 100 $Å^2$) play a decisive role for the functioning of silica as a thickening agent for liquids. It is through these silanol groups that the individual silica particles join together and form a three-dimensional network which changes into a firm gel structure with sufficient concentration. In what manner and to what degree the silanol and siloxane groups are responsible for the reinforcing mechanism in polymers, especially in silicone rubber, is still largely unknown. Analogous to considerations for elastomers containing carbon black, it may be assumed that when vulcanizing, no local chemical bonds form on the filler surface, but rather that physical absorption takes place which allows lateral movements along the particle surface.

The silanol groups are the sites on the surface where moisture can be absorbed. Therefore, silica normally is hydrophilic. As the silanol groups are reactive, they can be made ineffective by reacting them with organic or silicon-organic groups (e.g. dimethyl dichloro silane); in this way a hydrophobic and, at the same time, organophilic silica is obtained. Such a product is commercially available.

Whereas the silanol group density largely adjusts itself in the hydrolysis process (fortunately to the optimum degree for thickening purposes) and can only be varied within narrow limits in large-scale production, the BET surface area can be adjusted within the above-mentioned range. The most important application for these silicas is as thickening and thixotropic agent for liquid systems. In the plastics field, these are primarily laminating resins and gelcoats as well as resins used in sealants, adhesives, and plastisols. Another important application of silica not to be underestimated is its use as active, i.e., reinforcing, filler for silicone rubber.

As shown in FIG. 1, silica products produced by flame hydrolysis with generally different average surface area size distribution; e.g. 150 m$^2$/g, 200 m$^2$/g, 250 m$^2$/g, 300 m$^2$/g etc. can show the same thickening effects. The graph shows the thickening effect measured in 2% ludopol in 2 Pas.

Measuring the turbidity of solid dispersions in an inert liquid medium such as water is known in the art. It is based on the following physical concept:

The electrical field associated with incident light can stimulate a dipole to oscillate. An oscillating dipole itself emits scattered light, wherein the planes of vibration of the two beams are at right angles to each other. There is more short wavelength radiation in the scattered beam because the reciprocal of the fourth power of the wavelength is used in Rayleigh's Law. In the case of Rayleigh scattering, the particles must be smaller than the wavelength of the light (ca 1/20 of the wavelength). With these small particles the intensity of scattered light is almost independent of the angle of scattering. Larger particles scatter light virtually only in a forward direction. A 5 µm particle, for instance, scatters 100 times more light at a 25° angle than at a 90° angle. The intensity of light scattered at 90° passes through a maximum at a particle diameter of about 1 µm. This means, therefore, that large particles scatter less at 90° than smaller particles. To a first approximation, the refractive indices of all silicas produced by flame hydrolysis can be regarded as constant at ca 1.46. The known refractive index differences are produced by the particular dispersion medium. At large refractive index differences, as expected, there is a greater effect on turbidity. Assuming that the refractive index differences are constant and if the concentration is also kept constant, Rayleigh's equation simplifies to $I=k^*1/N$, where I is the scattered energy, k is a constant, and N is the number of particles per ml of solution.

Lord Rayleigh was the first to work out the dependence of the scattered flux density on frequency. In accord with $$I(\theta) = \frac{P_0^2 w^4}{32\pi^2 C^3 \epsilon_0} \frac{\sin^2\theta}{r^2}$$

which describes the radiation pattern for an oscillating dipole, the scattered flux density is directly proportional to the fourth power of the driving frequency. The scattering of light by objects which are small in comparison to the wavelength is known as Rayleigh scattering. The molecules of dense transparent media, be they gaseous, liquid or solid, will similarly scatter predominantly bluish light, if only feebly. The effect is quite weak particularly in liquids and solids because the oscillators are arrayed in a more orderly fashion and the re-emitted wavelets tend to reinforce each other only in the forward direction, canceling sideways scattering.

For a discussion of Rayleigh's law and the general subject see Jacobs, "Fundamentals of Optical Engineering" McGraw-Hill 1943, Chapter xxx, page 443 et seq; Perry, "Chemical Engineer's Handbook", McGraw-Hill p. 96 et seq; Hecht et al. "OPTICS" Addison-Wesley Publication Co. 1974 and Parker, "Optics Source Book" McGraw-Hill 1988, p. 222–224.

The process according to the invention has the advantage that reproducible correlations between the thickener effect of silica and the intensity of scattering can be determined. Methods for measuring turbidity can therefore be utilized to determine the thickening effect.

By obtaining a series of scattering determinations and measurements of thickening effect, a chart or data base can be prepared which can serve as a reference value or standard for comparing thickening effectiveness with turbidity values. Then to find the corresponding thickening effect, one need only identify the turbidity value. The data base will provide the corresponding thickening effectiveness value. This procedure can be done by simple chart or by computer. Then, in the course of commercial production of the flame-hydrolysis-produced silica, samples of the product can be taken at periodic intervals during or after production and subjected to the turbidity testing procedure of the present invention to obtain measurements of turbidity. The measured values of turbidity are then compared with the reference values and in that way a correlation can be made between the desired value for the thickening effectiveness and the measured turbidity value. In this way the effectiveness or thickening of the product can be determined. The process conditions can also be adjusted in the directions of producing the desired product.

Figure 3:
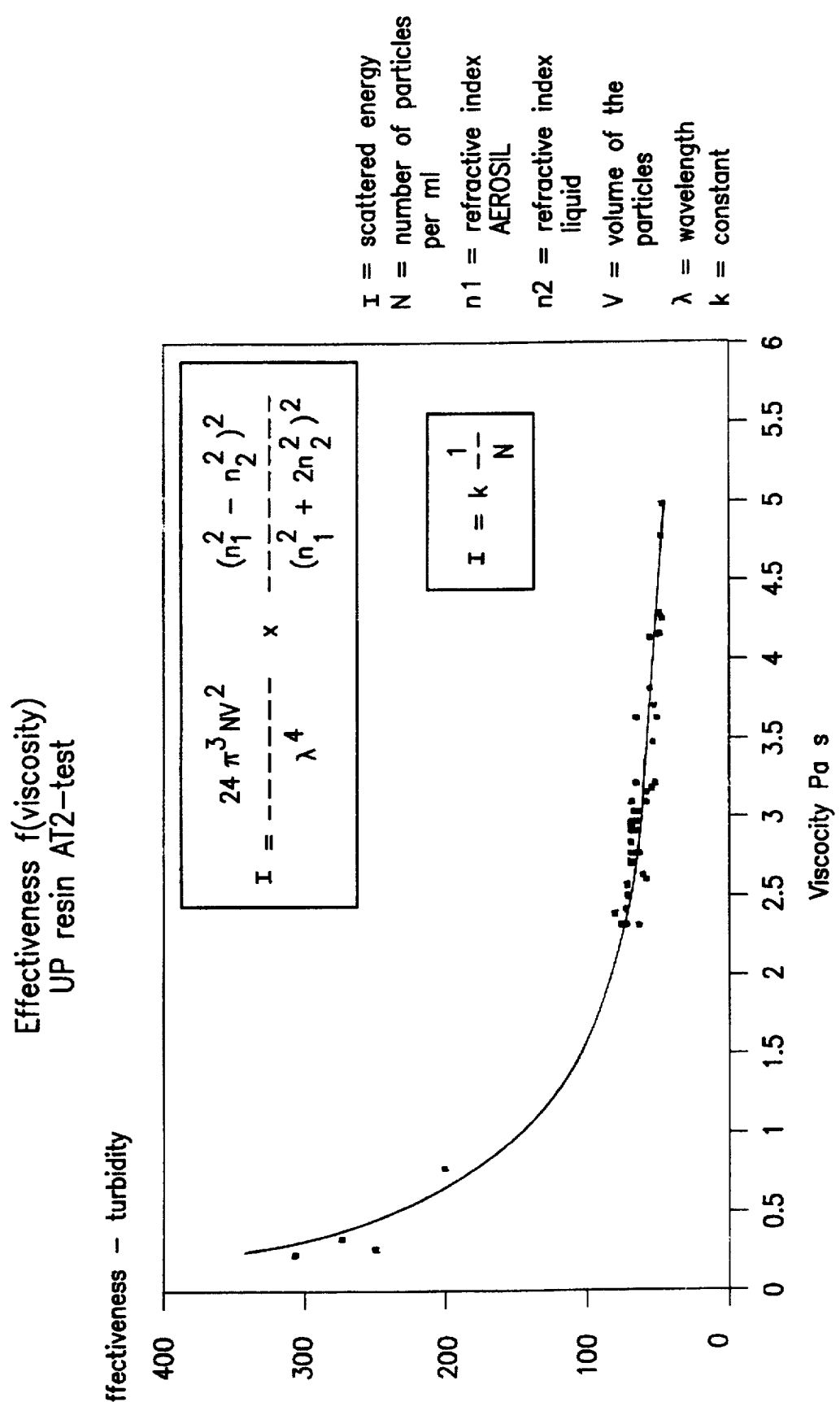
FIG. 3 is a plot of the turbidity measurements of different types of silica produced by flame hydrolysis.

As can be seen by the following example, the graph of the correlation between the thickening effect (viscosity) and the measured turbidity value must be made independently of concentration. Thus, the different types of silica, which are dispersed and used as the reference values in the chart in FIG. 3 are tested for the thickening effect (viscosity) and turbidity value at the same concentration. In this Example, a concentration of 1.00n g silica per 99.n g water is used as shown below. Due to the fact that the reference values for the silica dispersion were graphed using the same concentration, the thickening effects due to the concentration of silicon dioxide were eliminated. The elimination of this effect due to concentration is important because the concentration of the thickening agent, here silica, has an impact on the thickening effect. It is well-known in the art that the thickening effect will be greater if a greater amount of the same thickening agent is used. The thickening effect will be the same, however, if the same amount of the same thickening agent is used as illustrated in the Example.

EXAMPLE

A sample (ca 10 to 100 g) of flame hydrolysis produced silica, known commercially as AEROSIL® (Degussa AG) is homogenized by manual shaking (30 sec). The sample is weighed out at the earliest after 10 min (buoyancy). In order to compare an unknown sample to those values on the chart, the same concentration as the reference dispersions in FIG. 3 must be used. Therefore, the concentration of the unknown sample in this Example must be equal to 1.00 g of silica to 99 g of water. For example, the unknown sample can be 5 g of silica dispersed in 495 g of water. The preliminary homogenization step, mentioned above, is necessary to break up the silica aggregates that are formed in the silica powder itself before the powder is made into the dispersion.

1.00n g of the silica (AEROSIL®) and 99.n g of water for a hydrophilic silica or 99.n g of ethanol for a hydrophobic silica are weighed out (n=1–9) in a plastic beaker and dispersed using the dissolver for 5 minutes at 2000 rpm. After termination of the dispersion phase, the dispersion is dispensed into a disposable cell, using a Pasteur pipette, and the effectiveness is measured using a LTP 5 turbidity photometer from the Dr. Lange company. A lower alcohol can be used as the vehicle for hydrophobic silica.

The following equipment is required to perform the measurement:

| Equipment | Manufacturer |
|---|---|
| Laboratory dissolver LD 50 Ex 0.37 KW 930–8400 rpm Dispersion disc with welded hub, diameter 40 mm Hoechst can, Indent-No. 22926 250 ml volume, DD-PE, natural 0/00 | Pentraulik GmbH Maschinen und Apparate Philipp-Reis-Strasse Postfach 11 50 D-3257 Springe 1 Hoechst AG Abt. EK-Verpackung V 21 Brüningstrasse 64 D-6320 Frankfurt-Hoechst |
| Pasteur pipette; 3.5 ml 150 mm long, order no. 1-6151 | Oskar Glock GmbH & Co. KG Labortechnik Postfach 10 06 61 D-6050 Offenbach |
| Lange turbidity photometer LTP 5, item no. LPV 138 1 adapter, item no. BHA 074 1000 cells, item no. EBK 019 | Dr. Bruno Lange GmbH Königsweg 10 Postfach 37 03 63 D-1000 Berlin 37 |

Figure 2:
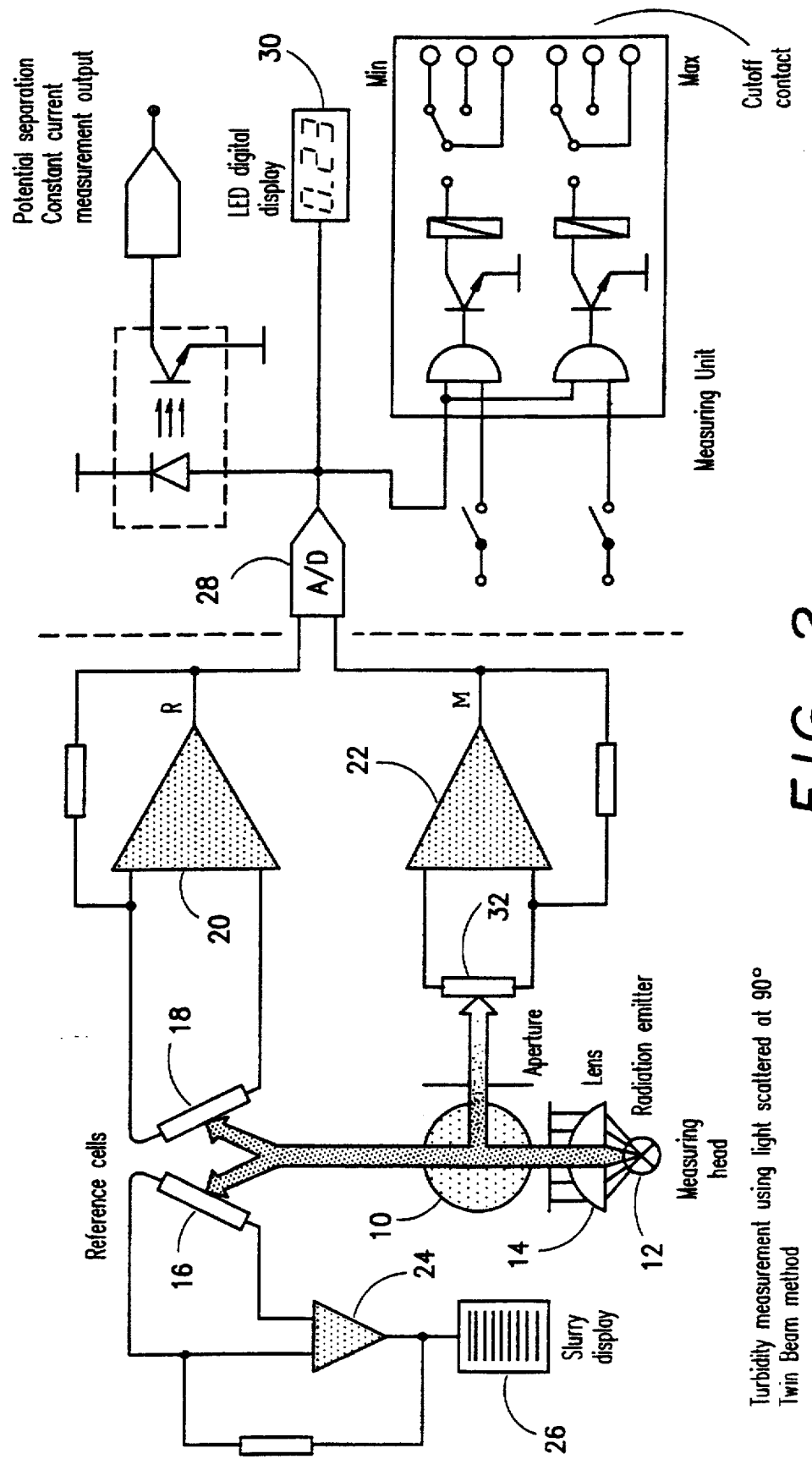
FIG. 2 is a schematic diagram of a typical turbidity photometer suitable for use in the present invention.

A schematic diagram of the turbidity photometer used according to the invention is given in FIG. 2. The sample 10 for testing is placed in a beam from light source 12 focused by lens 14. Light emitted at 180° C. passes straight through the dispersion sample 10 and is detected by light detectors 16, 18. Light deflected at 90° C. is passed to detector 32. The signals from the light detectors are amplified by amplifiers 20 and 22. The signal from detector 16 is sent to amplifier 24 and on to slurry display 26. The combined analog signals are converted by convertor 28 to a digital signal which is conveyed to LED display 30.

The results of the turbidity measurement for different types of AEROSIL® brand silica are given graphically in FIG. 3. This graph demonstrates a clear correlation between the thickening effect and the intensity of the turbidity measurement. This correlation forms the standard to which the unknown sample is compared. To find the thickening effect of the unknown sample, the following steps are taken. The turbidity of the unknown sample is measured at the same concentration as the silica dispersions used for the reference values in a correlation graph such as FIG. 3. Then one simply looks to the ordinate for the turbidity measurement of the unknown sample. The corresponding value for the thickening effect (viscosity) is read from the abscissa. Thus, the thickening effect (viscosity) of the sample can be determined by merely measuring its turbidity.

Further modifications and variations will be apparent to those skilled in the art from reading the foregoing and are intended to be encompassed by the claims appended hereto.

German priority application P 44 00 170.3 is relied on and incorporated herein by reference.

We claim:

1. A process for determining the thickening effect of a silicon dioxide, which has been produced by flame hydrolysis comprising taking a known quantity of a flame hydrolysis produced silicon dioxide;

forming a sample dispersion thereof from said known quantity of said silicon dioxide in an inert liquid medium;

obtaining a turbidity measurement of said sample dispersion;

corresponding said turbidity measurement of said sample dispersion with a previously prepared standard;

said previously prepared standard being a correlation of a series of turbidity measurements as a function of thickening effect using dispersions of different silicas, each of said dispersions of different silicas having the same concentration; and said sample dispersion having the same concentration of silica as each of said dispersions of different silicas.

2. The process according to claim 1 wherein water is the medium.

3. The process according to claim 1 wherein ethanol is the medium.

4. The process according to claim 1 wherein obtaining the turbidity of measurement of said sample dispersion comprises sending a light beam through said sample dispersion;

measuring the light deflected at 90° C. and emitted at 180° C. with respect to the light source through said sample dispersion; and comparing the signals so obtained.

5. A process for determining the thickening effect of a silicon dioxide which has been produced by flame hydrolysis in order to provide reliable quality control of the resulting silicon dioxide comprising taking a known quantity of a flame hydrolysis produced silicon dioxide, prepared in the course of commercial production;

forming a sample dispersion thereof from said known quantity of said silicon dioxide in an inert liquid medium;

obtaining a turbidity measurement of said sample dispersion;

corresponding said turbidity measurement of said sample dispersion with a previously prepared standard;

wherein said previously prepared standard is a correlation of a series of turbidity measurements as a function of thickening effect using dispersions of different silicas, each of said dispersions of different silicas having the same concentration;

said sample dispersion having the same concentration of silica as each of said dispersions of different silicas;

thereby evaluating the capability of the silicon dioxide to act as a suitable thickening agent.

6. The process according to claim 5 wherein said corresponding is carried out by obtaining a correlation between the thickening effect of silica and the intensity of scattering of light.

7. The process according to claim 5 wherein turbidity measurement of said sample dispersion is measured by measuring the intensity of light scattered as the light passes through said sample dispersion of said silicon dioxide dispersed in said inert liquid medium.

8. The process according to claim 5 wherein said previously prepared standard comprises a table, chart or database prepared from a series of scattering determinations and measurements of thickeninq effect that is used to compare thickening effectiveness with turbidity values.

9. The process according to claim 8 wherein the thickening effect is determined by identifying the turbidity value and comparing it with the standard table, chart or database containing a series of scattering determinations and measurements of thickening effect.

* * * * *

UNITED STATES PATENT AND TRADEMARK OFFICE
CERTIFICATE OF CORRECTION

PATENT NO.  : 5,736,407
DATED       : April 7, 1998
INVENTOR(S) : Hennig, et. al.

It is certified that error appears in the above-indentified patent and that said Letters Patent is hereby corrected as shown below:

Title page, item [75], inventor:   change "Henning" to --Hennig--.

Signed and Sealed this

Fourth Day of August, 1998

Attest:

BRUCE LEHMAN

Attesting Officer          Commissioner of Patents and Trademarks